United States Patent [19]

Asao et al.

[11] 4,237,122
[45] Dec. 2, 1980

[54] IMIDAZOLIDINEDIONE COMPOUNDS, AND THEIR PRODUCTION AND USE

[75] Inventors: Shuichiro Asao, Ashiya; Shigeo Yamamoto, Ikeda; Yoshio Hisada, Kawanishi; Yoshinori Nakayama, Takarazuka; Chiyozo Takayama, Toyonaka, all of Japan

[73] Assignee: Sumitomo Chemical Company, Limited, Osaka, Japan

[21] Appl. No.: 48,745

[22] Filed: Jun. 15, 1979

[30] Foreign Application Priority Data

Jun. 22, 1978 [JP] Japan .................................. 53-76109
Dec. 28, 1978 [JP] Japan .................................. 53-163012

[51] Int. Cl.³ .................... A01N 57/16; C07D 233/40
[52] U.S. Cl. ..................................... 424/200; 548/111
[58] Field of Search ............... 260/309.5; 424/200; 548/111

[56] References Cited

U.S. PATENT DOCUMENTS 3,734,890  5/1973  Pallos ................................ 260/944
3,912,495  10/1975  Moser ................................... 71/90

FOREIGN PATENT DOCUMENTS 7466829  10/1972  Japan .

*Primary Examiner*—Donald G. Daus
*Assistant Examiner*—Lisa Jones
*Attorney, Agent, or Firm*—Birch, Stewart, Kolasch & Birch

[57] ABSTRACT

An imidazolidinedione compound of the formula:

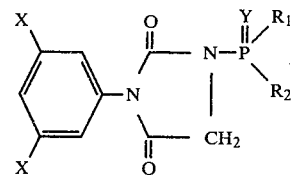

wherein X is a chlorine atom or a bromine atom, Y is an oxygen atom or a sulfur atom, and $R_1$ and $R_2$ are each a $C_1$-$C_4$ alkyl group, a $C_1$-$C_4$ alkoxy group, a $C_1$-$C_4$ alkylthio group, an ar($C_1$-$C_4$)alkylthio group, a $C_1$-$C_4$ alkoxy($C_2$-$C_4$)alkoxy group, a phenyl group, a phenoxy group, a $C_1$-$C_4$ alkylthiophenoxy group, a $C_1$-$C_8$ alkylamino group, a $C_2$-$C_8$ alkenylamino group or a cyano($C_1$-$C_4$)alkylamino group, which is useful as an agricultural chemical such as insecticides, acaricides, nematocides and/or fungicides with high safety to mammalian animals and human beings.

13 Claims, No Drawings

IMIDAZOLIDINEDIONE COMPOUNDS, AND THEIR PRODUCTION AND USE

The present invention relates to imidazolidinedione compounds, and their production and use.

The said imidazolidinedione compounds are representable by the formula:

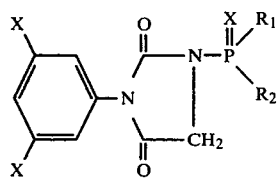

wherein X is a chlorine atom or a bromine atom, Y is an oxygen atom or a sulfur atom, and $R_1$ and $R_2$ are each a $C_1$–$C_4$ alkyl group, a $C_1$–$C_4$ alkoxy group, a $C_1$–$C_4$ alkylthio group, an ar($C_1$–$C_4$)alkylthio group, a $C_1$–$C_4$ alkoxy($C_2$–$C_4$)alkoxy group, a phenyl group, a phenoxy group, a $C_1$–$C_4$ alkylthiophenoxy group, a $C_1$–$C_8$ alkylamino group, a $C_2$–$C_8$ alkenylamino group or a cyano($C_1$–$C_4$)alkylamino group.

It has been found that the imidazolidinedione compounds (I) have various useful activities as agricultural chemicals. For instance, they exhibit a remarkable controlling activity against harmful insects belonging to Hemiptera, Diptera, Lepidoptera, etc. as well as acarids and nematodes parasitic to plants. Their high killing potency against rice stem borers and red spiders is particularly notable. Due to their penetrating transfer property, they are usable as insecticides for treatment of soil. Further, for instance, they have an excellent preventive effect to a wide variety of phyto-pathogenic fungi. It is notable that they show fungal activity not only against wild organisms (i.e. sensitive organisms) but also against organisms tolerant to conventional fungicides. Examples of the phyto-pathogenic fungi on which their excellent preventive effect is observed are *Alternaria kikuchiana* (black spot), *Alternaria mali* (Alternaria leaf spot), *Venturia inaequalis* (scab), *Valsa mali* (canker), *Sclerotinia mali* (blossom blight), *Elsinoe fawcetti* (scab), *Diaporthe citri* (Melanose), *Penicillium italicum* (blue mould), *Penicillium digitatum* (common green mould), *Sclerotinia cinerea* (brown rot), *Glomerella cingulata* (ripe rot), *Gloeosporium kaki* (Anthracnose), *Colletotrichum lagenarium* (Anthracnose), *Pseudo-peronospora cubensis* (downy mildew), *Phytophthora infestans* (late blight), *Alternaria solani* (early blight), *Sclerotinia sclerotiorum* (Sclerotinia rot), *Botrytis cinerea* (gray mould), *Alternaria brassicicola* (Alternaria sooty spot), *Pyricularia oryzae* (rice blast), *Rhizoctonia solani* (sheath blight), etc. Among these fungi, their remarkable effect against *Valsa mali* is highly notable. It is advantageous that when they are applied to rice plants, the preventive effect to rice blast and sheath blight and the inhibitory or killing effect to rice stem borers can be simultaneously expected. Advantageously, the imidazolidinedione compounds (I) show only a very weak toxicity against mammals.

Accordingly, the imidazolidinedione compounds (I) are useful as agricultural chemicals such as insecticides, acaricides, nematocides and fungicides with high safety to mammalian animals and human beings.

The imidazolidinedione compounds (I) can be prepared by reacting a 3-(3,5-dihalophenyl)imidazolidinedione compound of the formula:

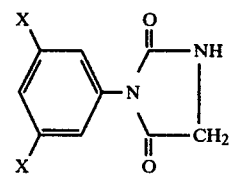

wherein X is as defined above with a phosphoryl halide of the formula:

wherein Z is a chlorine atom or a bromine atom and $R_1$, $R_2$ and Y are each as defined above.

The reaction is usually effected by treatment of the compound (II) with the compound (III) in a molar ratio of 1:1.0–5.0, preferably of 1:1.0–2.0, in the presence or absence of a proper solvent (e.g. diethyl ether, tetrahydrofuran, 1,2-dimethoxyethane, diglyme) in the presence of a hydrogen halide-eliminating agent such as an alkali metal (e.g. metallic sodium), an alkali hydride (e.g. sodium hydride) or an alkali alkoxide (e.g. sodium methoxide, sodium ethoxide) at a temperature of $-20°$ to $100°$ C., preferably of $-10°$ to $50°$ C., if desired, while stirring. The amount of proper solvent may be, when used, from 1 to 1000 parts by weight to one part by weight of the compound (II). Further, the amount of the hydrogen halide-eliminating agent may be from 1 to 2 moles to 1 mole of the compound (II). The reaction can be accomplished instantaneously or within about 48 hours, usually from about 1 to 18 hours, under the said conditions.

Some typical embodiments of the process for preparing the imidazolidinedione compounds (I) according to this invention are as follows:

EXAMPLE 1

A solution of 3-(3,5-dichlorophenyl)imidazolidine-2,4-dione (0.05 mole) in tetrahydrofuran was cooled to a temperature below 10° C., sodium hydride (0.06 mole) was gradually added thereto, and the resultant mixture was stirred at 20° C. for 1 hour. After the dropwise addition of O,O-dimethylthionophosphoryl chloride (0.05 mole) under cooling with water, the resulting mixture was stirred at 20° C. for 17 hours. The reaction mixture was poured into ice-water and extracted with ether. The ether extract was washed with dilute hydrochloric acid, aqueous sodium bicarbonate solution and water in order and dried over magnesium sulfate, followed by filtration. The filtrate was concentrated to evaporate the ether and subjected to column chromatography, whereby 1-(O,O-dimethylthionophosphoryl)-3-(3,5-dichlorophenyl)imidazolidine-2,4-dione (11.0 g) was obtained. Yield, 61%.

EXAMPLE 2

A solution of 3-(3,5-dichlorophenyl)imidazolidine-2,4-dione (0.04 mole) in tetrahydrofuran was cooled to a temperature below 10° C., sodium hydride (0.05 mole) was gradually added thereto, and the resultant mixture was stirred at 20° C. for 2 hours. After the dropwise addition of diethylchlorophosphate (0.04 mole) under cooling with water, the resulting mixture was stirred at 20° C. for 13 hours. The reaction mixture was poured into ice-water and extracted with chloroform. The chloroform extract was washed with dilute hydrochloric acid, aqueous sodium bicarbonate solution and water in order and dried over magnesium sulfate, followed by filtration. The filtrate was concentrated to evaporate the chloroform and subjected to column chromatography, whereby 1-(O,O-diethylphosphoryl)-3-(3,5-dichlorophenyl)imidazolidine-2,4-dione (7.8 g) was obtained. Yield, 51%.

EXAMPLE 3

A solution of 3-(3,5-dichlorophenyl)imidazolidine-2,4-dione (0.05 mole) in dioxane was cooled to a temperature below 10° C., sodium hydride (0.06 mole) was gradually added thereto, and the resultant mixture was stirred at 20° C. for 2 hours. After the dropwise addition of O-ethyl-S-(2-phenylethyl)thionochlorophosphate (0.05 mole) under cooling with water, the resulting mixture was stirred at 20° C. for 14 hours. The reaction mixture was poured into ice-water and extracted with ether. The ether extract was washed with dilute hydrochloric acid, aqueous sodium bicarbonate solution and water in order and dried over magnesium sulfate, followed by filtration. The filtrate was concentrated to evaporate the ether and subjected to column chromatography, whereby 1[O-ethyl-S-(2-phenylethyl)thionophosphoryl]-3-(3,5-dichlorophenyl)imidazolidine-2,4-dione (12.5 g) was obtained. Yield, 51%.

In the same manner as above, the following imidazolidinedione compounds (I) are obtained by the reaction between 3-(3,5-dichlorophenyl)imidazolidine-2,4-dione (II: X=Cl) and the phosphoryl halide (III):

TABLE 1

| Phosphoryl halide (III) | Compound No. | Chemical structure | Physical constant | Yield (%) | Elementary analysis (%) | | | | | |
|---|---|---|---|---|---|---|---|---|---|---|
| | | | | | C | H | N | Cl | P | S |
| CH₃O—P(=S)(Cl)—OCH₃ | 1 | (3,5-Cl₂C₆H₃)N-imidazolidinedione with N—P(=S)(OCH₃)₂ | $n_D^{23.7}$ 1.5842 | 61 | 35.79 (35.87) | 3.00 (3.13) | 7.59 (7.77) | 19.21 (19.46) | 8.39 (8.53) | 8.69 (8.45) |
| C₂H₅O—P(=S)(Cl)—OC₂H₅ | 2 | (3,5-Cl₂C₆H₃)N-imidazolidinedione with N—P(=S)(OC₂H₅)₂ | $n_D^{23.0}$ 1.5612 | 30 | 39.31 (39.60) | 3.81 (3.83) | 7.05 (6.81) | 17.85 (17.82) | 7.80 (7.65) | 8.07 (7.83) |
| C₂H₅O—P(=O)(Cl)—OC₂H₅ | 3 | (3,5-Cl₂C₆H₃)N-imidazolidinedione with N—P(=O)(OC₂H₅)₂ | $n_D^{23.7}$ 1.5470 | 51 | 40.97 (40.72) | 3.97 (4.14) | 7.35 (7.08) | 18.60 (18.48) | 8.13 (7.99) | — (—) |
| (n)C₄H₉O—P(=O)(Cl)—OC₄H₉(n) | 4 | (3,5-Cl₂C₆H₃)N-imidazolidinedione with N—P(=O)(OC₄H₉(n))₂ | $n_D^{23.0}$ 1.5256 | 73 | 54.24 (54.17) | 4.55 (4.64) | 5.50 (5.62) | 13.92 (13.80) | 6.08 (6.20) | — (—) |
| C₂H₅O—P(=S)(Cl)—OC₆H₅ | 5 | (3,5-Cl₂C₆H₃)N-imidazolidinedione with N—P(=S)(OC₂H₅)(OC₆H₅) | M.P., 93.5–94.5° C. | 53 | 45.86 (45.57) | 3.40 (3.37) | 6.29 (6.16) | 15.92 (15.94) | 6.96 (6.72) | 7.20 (6.93) |

TABLE 1-continued

| Phosphoryl halide (III) | Compound No. | Chemical structure | Physical constant | Yield (%) | Elementary analysis (%) C | H | N | Cl | P | S |
|---|---|---|---|---|---|---|---|---|---|---|
| $C_2H_5O$, $S$, $P-Cl$, $O-C_6H_4-SCH_3$ | 6 | (structure with S=P(OC_2H_5)(O-C_6H_4-SCH_3), N-imidazolidinedione, 3,5-dichlorophenyl) | $n_D^{26.0}$ 1.5935 | 33 | 44.00 (44.17) | 3.49 (3.38) | 5.70 (5.45) | 14.43 (14.17) | 6.30 (6.17) | 13.05 (13.11) |
| $CH_3NH$, $S$, $P-Cl$, $CH_3O$ | 7 | (structure with S=P(NHCH_3)(OCH_3)) | M.P., 158.0–158.5° C. | 43 | 35.89 (35.99) | 3.29 (3.43) | 11.41 (11.52) | 19.26 (19.38) | 8.41 (8.21) | 8.71 (8.82) |
| $(n)C_6H_{13}NH$, $S$, $P-Cl$, $CH_3O$ | 8 | (structure with S=P(NHC_6H_{13}(n))(OCH_3)) | $n_D^{26.0}$ 1.5569 | 37 | 43.84 (44.03) | 5.06 (5.27) | 9.59 (9.54) | 16.18 (16.32) | 7.07 (6.82) | 7.32 (7.40) |
| $(iso)C_3H_7NH$, $S$, $P-Cl$, $C_2H_5O$ | 9 | (structure with S=P(NHC_3H_7(iso))(OC_2H_5)) | M.P., 155.0–156.5° C. | 40 | 40.99 (40.74) | 4.42 (4.47) | 10.24 (10.48) | 17.28 (17.17) | 7.55 (7.45) | 7.82 (8.07) |
| $CH_3NH$, $S$, $P-Cl$, $C_2H_5O$ | 10 | (structure with S=P(NHCH_3)(OC_2H_5)) | M.P., 110.5–111.5° C. | 34 | 37.71 (37.43) | 3.69 (3.82) | 10.99 (11.16) | 18.55 (18.34) | 8.10 (8.18) | 8.39 (8.43) |

TABLE 1-continued

| Phosphoryl halide (III) | Compound No. | Produced imidazolidinedione compound (I) Chemical structure | Physical constant | Yield (%) | Elementary analysis (%) C | H | N | Cl | P | S |
|---|---|---|---|---|---|---|---|---|---|---|
| (sec)C₄H₉NH–P(=S)(Cl)(OC₂H₅) | 11 | [3,5-dichlorophenyl imidazolidinedione with S=P(NHC₄H₉(sec))(OC₂H₅)] | M.P., 112.5–114.5° C. | 32 | 42.46 (42.49) | 4.75 (4.68) | 9.90 (9.78) | 16.71 (16.74) | 7.30 (7.28) | 7.56 (7.25) |
| CH₃CH₂S–P(=S)(Cl)(OC₂H₅) via CH₂ phenyl | 12 | [3,5-dichlorophenyl imidazolidinedione with S=P(SCH₂CH₂C₆H₅)(OC₂H₅)] | $n_D^{26.0}$ 1.6026 | 51 | 46.63 (46.79) | 3.91 (4.18) | 5.72 (5.70) | 14.49 (14.61) | 6.33 (6.52) | 13.10 (13.36) |
| C₆H₅S–P(=S)(Cl)(OC₂H₅) | 13 | [3,5-dichlorophenyl imidazolidinedione with S=P(SC₆H₅)(OC₂H₅)] | $n_D^{26.0}$ 1.5860 | 73 | 47.57 (47.70) | 3.52 (3.60) | 6.53 (6.50) | 16.52 (16.24) | 7.22 (7.00) | 7.47 (7.49) |
| (sec)C₄H₉S–P(=S)(Cl)(OC₂H₅) | 14 | [3,5-dichlorophenyl imidazolidinedione with S=P(SC₄H₉(sec))(OC₂H₅)] | $n_D^{24.7}$ 1.5879 | 52 | 40.82 (40.69) | 4.34 (4.38) | 6.35 (6.58) | 16.07 (16.23) | 7.02 (7.22) | 14.53 (14.54) |
| CH₃OCH₂CH₂O–P(=O)(Cl)(C₆H₅) | 15 | [3,5-dichlorophenyl imidazolidinedione with O=P(OCH₂CH₂OCH₃)(C₆H₅)] | $n_D^{22.5}$ 1.5609 | 46 | 48.78 (48.58) | 3.87 (4.02) | 6.32 (6.05) | 16.00 (15.89) | 6.99 (6.75) | — — |

TABLE 1-continued

| Phosphoryl halide (III) | Compound No. | Chemical structure | Physical constant | Yield (%) | Elementary analysis (%) C | H | N | Cl | P | S |
|---|---|---|---|---|---|---|---|---|---|---|
| (CH₃)₂N—P(=O)(N(CH₃)₂)—Cl | 16 | 3,5-dichlorophenyl imidazolidinedione with P(=O)(N(CH₃)₂)₂ | $n_D^{23.0}$ 1.5407 | 43 | 41.18 (41.17) | 4.52 (4.55) | 14.78 (14.86) | 18.70 (18.96) | 8.17 (8.35) | — — |
| (iso)C₃H₇NH—P(=S)(C₂H₅)—Cl | 17 | 3,5-dichlorophenyl imidazolidinedione with P(=S)(NHC₃H₇(iso))(C₂H₅) | M.P., 135.5–137.0° C. | 35 | 42.65 (42.93) | 4.60 (4.78) | 10.66 (10.69) | 17.98 (17.79) | 7.86 (7.98) | 8.13 (8.35) |
| NCCH₂CH₂NH—P(=S)(OC₂H₅)—Cl | 18 | 3,5-dichlorophenyl imidazolidinedione with P(=S)(NHCH₂CH₂CN)(OC₂H₅) | M.P., 135.0–136.5° C. | 27 | 39.92 (40.06) | 3.59 (3.56) | 13.30 (13.12) | 16.83 (17.06) | 7.35 (7.23) | 7.61 (7.34) |
| CH₂=CHCH₂NH—P(=S)(CH₃O)—Cl | 19 | 3,5-dichlorophenyl imidazolidinedione with P(=S)(NHCH₂CH=CH₂)(OCH₃) | $n_D^{26.0}$ 1.5761 | 30 | 39.61 (39.62) | 3.58 (3.30) | 10.66 (10.91) | 17.99 (18.00) | 7.86 (8.09) | 8.13 (8.42) |
| (iso)C₃H₇NH—P(=S)(NHC₃H₇(n))—Cl | 20 | 3,5-dichlorophenyl imidazolidinedione with P(=S)(NHC₃H₇(iso))(NHC₃H₇(n)) | M.P., 119.5–121.0° C. | 26 | 42.56 (42.55) | 5.00 (5.18) | 13.24 (13.24) | 16.75 (16.88) | 7.32 (7.49) | 7.57 (7.70) |

TABLE 1-continued

Produced imidazolidinedione compound (I)

| Phosphoryl halide (III) | Compound No. | Chemical structure | Physical constant | Yield (%) | Elementary analysis (%) | | | | | |
|---|---|---|---|---|---|---|---|---|---|---|
| | | | | | C | H | N | Cl | P | S |
| CH₃O S<br>\\ ∥<br>P—Cl<br>/<br>CH₃O | 21 | S OCH₃<br>∥ /<br>P<br>/ \\ OCH₃<br>N<br>O= =O<br>N<br>[3,5-Br₂-C₆H₃] | $n_D^{23.0}$ 1.5921 | 42 | 28.84 (28.71) | 2.42 (2.20) | 6.12 (6.35) | 34.89 (34.97) | 6.76 (6.53) | 7.00 (7.21) |
| (n)C₃H₇S S<br>\\ ∥<br>P—Cl<br>/<br>C₂H₅O | 22 | S SC₃H₇(n)<br>∥ /<br>P<br>/ \\ OC₂H₅<br>N<br>O= =O<br>N<br>[3,5-Cl₂-C₆H₃] | $n_D^{23.2}$ 1.5782 | 54 | 39.35 (39.20) | 4.01 (3.88) | 6.56 (6.73) | 16.59 (16.50) | 7.25 (7.03) | 15.01 (15.21) |
| (i)C₃H₇O S<br>\\ ∥<br>P—Cl<br>/<br>(i)C₃H₇O | 23 | S OC₃H₇(i)<br>∥ /<br>P<br>/ \\ OC₃H₇(i)<br>N<br>O= =O<br>N<br>[3,5-Cl₂-C₆H₃] | $n_D^{23.5}$ 1.5437 | 45 | 45.81 (45.75) | 4.87 (5.02) | 7.12 (7.12) | 18.03 (17.84) | 7.88 (8.09) | 8.15 (8.35) |
| C₂H₅O(CH₂)₄O O<br>\\ ∥<br>P—Cl<br>/<br>C₆H₅ | 24 | O O(CH₂)₄OC₂H₅<br>∥ /<br>P<br>/ \\ C₆H₅<br>N<br>O= =O<br>N<br>[3,5-Cl₂-C₆H₃] | $n_D^{24.0}$ 1.5421 | 52 | 50.31 (50.16) | 4.62 (4.45) | 5.59 (5.74) | 14.14 (14.03) | 6.18 (6.34) | 6.40 (6.65) |
| (n)C₃H₇O(CH₂)₃O S<br>\\ ∥<br>P—Cl<br>/<br>C₂H₅N<br>H | 25 | S O(CH₂)₃OC₃H₇(n)<br>∥ /<br>P<br>/ \\ NC₂H₅<br>N H<br>O= =O<br>N<br>[3,5-Cl₂-C₆H₃] | $n_D^{24.5}$ 1.5475 | 33 | 43.60 (43.62) | 5.17 (4.96) | 8.97 (9.03) | 15.14 (15.18) | 6.61 (6.58) | 6.85 (6.99) |

TABLE 1-continued

| Compound No. | Phosphoryl halide (III) | Produced imidazolidinedione compound (I) Chemical structure | Physical constant | Yield (%) | Elementary analysis (%) C | H | N | Cl | P | S |
|---|---|---|---|---|---|---|---|---|---|---|
| 26 | (sec)C$_4$H$_9$O(CH$_2$)$_2$O, O=P-Cl, C$_6$H$_5$ | [structure with S=P(O(CH$_2$)$_2$OC$_4$H$_9$(sec))(C$_6$H$_5$) attached to N of imidazolidinedione with 3,5-dichlorophenyl] | $n_D^{24.0}$ 1.5461 | 47 | 50.31 (50.41) | 4.62 (4.79) | 5.59 (5.58) | 14.14 (13.99) | 6.18 (6.28) | 6.40 (6.27) |
| 27 | C$_2$H$_5$S—C$_6$H$_4$—O, S=P-Cl, C$_2$H$_5$O | [structure with S=P(OC$_6$H$_4$SC$_2$H$_5$)(OC$_2$H$_5$)] | $n_D^{25.0}$ 1.5031 | 35 | 45.16 (45.23) | 3.79 (3.86) | 5.54 (5.51) | 14.03 (14.17) | 6.13 (6.26) | 12.69 (12.57) |
| 28 | (t)C$_4$H$_9$S—C$_6$H$_4$—O, S=P-Cl, C$_2$H$_5$O | [structure with S=P(OC$_6$H$_4$SC$_4$H$_9$(t))(OC$_2$H$_5$)] | $n_D^{25.0}$ 1.4257 | 28 | 47.28 (47.32) | 4.35 (4.42) | 5.25 (5.30) | 13.29 (13.26) | 5.81 (5.93) | 12.02 (12.00) |
| 29 | (n)C$_3$H$_7$, C$_2$H$_5$, N, S=P-Cl, CH$_3$ | [structure with S=P(N(C$_3$H$_7$(n))(C$_2$H$_5$))(CH$_3$)] | $n_D^{24.0}$ 1.5926 | 38 | 44.13 (44.14) | 4.94 (4.95) | 10.29 (10.37) | 17.37 (17.23) | 7.59 (7.68) | 7.85 (8.01) |
| 30 | H, (n)C$_4$H$_9$N, S=P-Cl, (n)C$_4$H$_9$ | [structure with S=P(NHC$_4$H$_9$(n))(C$_4$H$_9$(n))] | $n_D^{24.0}$ 1.5637 | 42 | 46.80 (46.77) | 5.54 (5.55) | 9.63 (9.80) | 16.25 (16.44) | 7.10 (7.11) | 7.35 (7.48) |

TABLE 1-continued

| Phosphoryl halide (III) | Compound No. | Chemical structure | Physical constant | Yield (%) | C | H | N | Cl | P | S |
|---|---|---|---|---|---|---|---|---|---|---|
| H<br>CH₂=CHCH₂CH₂N  S<br>   ‖<br>   P—Cl<br>CH₃O | 31 | (3,5-dichlorophenyl-imidazolidinedione with S=P(OCH₃)(NHCH₂CH₂CH=CH₂)) | $n_D^{25.0}$ 1.4831 | 26 | 41.19 (41.19) | 3.95 (3.86) | 10.29 (10.12) | 17.37 (17.38) | 7.59 (7.64) | 7.85 (7.91) |
| (CH₂=CHCH₂)₂N  S<br>      ‖<br>      P—Cl<br>CH₃O | 32 | (3,5-dichlorophenyl-imidazolidinedione with S=P(OCH₃)(N(CH₂CH=CH₂)₂)) | $n_D^{25.0}$ 1.4257 | 22 | 44.25 (44.19) | 4.18 (4.06) | 9.68 (9.68) | 16.33 (16.32) | 7.13 (7.00) | 7.38 (7.35) |
| H<br>NCCH₂N  S<br>   ‖<br>   P—Cl<br>(i)C₃H₇O | 33 | (3,5-dichlorophenyl-imidazolidinedione with S=P(OC₃H₇(i))(NHCH₂CN)) | $n_D^{25.0}$ 1.5893 | 25 | 39.92 (40.07) | 3.59 (3.44) | 13.30 (13.22) | 16.83 (16.83) | 7.35 (7.45) | 7.61 (7.77) |
| H<br>NC(CH₂)₄N  S<br>   ‖<br>   P—Cl<br>C₂H₅O | 34 | (3,5-dichlorophenyl-imidazolidinedione with S=P(OC₂H₅)(NH(CH₂)₄CN)) | $n_D^{25.0}$ 1.5382 | 28 | 42.77 (42.70) | 4.26 (4.18) | 12.47 (12.32) | 15.78 (15.89) | 6.89 (6.93) | 7.14 (7.16) |
| (NCCH₂)₂N  S<br>      ‖<br>      P—Cl<br>C₂H₅O | 35 | (3,5-dichlorophenyl-imidazolidinedione with S=P(OC₂H₅)(N(CH₂CN)₂)) | $n_D^{25.0}$ 1.5713 | 20 | 40.37 (40.40) | 3.16 (3.14) | 15.69 (15.67) | 15.89 (15.94) | 6.94 (7.09) | 7.19 (7.03) |

TABLE 1-continued
Produced imidazolidinedione compound (I)

| Phosphoryl halide (III) | Compound No. | Chemical structure | Physical constant | Yield (%) | Elementary analysis (%) | | | | | |
|---|---|---|---|---|---|---|---|---|---|---|
| | | | | | C | H | N | Cl | P | S |
| CH₃S\P(=S)(Cl)(OC₄H₉(sec)) | 36 | [3,5-Cl₂C₆H₃-imidazolidinedione-N-P(=S)(SCH₃)(OC₄H₉(sec))] | $n_D^{25.0}$ 1.4892 | 46 | 39.35 (39.38) | 4.01 (4.11) | 6.56 (6.48) | 16.59 (16.66) | 7.25 (7.36) | 15.01 (14.92) |
| C₂H₅S\P(=S)(Cl)(OC₂H₅) | 37 | [3,5-Cl₂C₆H₃-imidazolidinedione-N-P(=S)(SC₂H₅)(OC₂H₅)] | $n_D^{25.0}$ 1.5925 | 53 | 37.78 (37.82) | 3.66 (3.75) | 6.78 (6.73) | 17.16 (17.23) | 7.49 (7.28) | 15.52 (15.38) |
| C₆H₅CH₂S\P(=S)(Cl)(OC₂H₅) | 38 | [3,5-Cl₂C₆H₃-imidazolidinedione-N-P(=S)(SCH₂C₆H₅)(OC₂H₅)] | $n_D^{25.0}$ 1.6137 | 47 | 45.48 (45.52) | 3.60 (3.76) | 5.89 (5.80) | 14.92 (14.94) | 6.52 (6.55) | 13.49 (13.52) |
| C₆H₅(CH₂)₂S\P(=S)(Cl)(OC₂H₅) | 39 | [3,5-Cl₂C₆H₃-imidazolidinedione-N-P(=S)(S(CH₂)₂C₆H₅)(OC₂H₅)] | $n_D^{25.0}$ 1.5237 | 43 | 48.75 (48.86) | 4.48 (4.56) | 5.41 (5.29) | 13.70 (13.67) | 5.99 (6.06) | 12.39 (12.46) |
| C₆H₅(CH₂)₃S\P(=S)(Cl)(OC₂H₅) | 40 | [3,5-Cl₂C₆H₃-imidazolidinedione-N-P(=S)(S(CH₂)₃C₆H₅)(OC₂H₅)] | $n_D^{25.5}$ 1.5739 | 39 | 47.72 (47.60) | 4.20 (4.18) | 5.56 (5.61) | 14.09 (14.25) | 6.15 (5.97) | 12.74 (12.79) |

Note:
In the elementary analysis, the values as calculated are unparenthesized, and the values as found are parenthesized.

For the use of the imidazolidinedione compound (I) as an agricultural chemical such as an insecticide, an acaricide, a nematocide or a fungicide, it is usually extended with a suitable carrier or diluent, if desired, by the aid of an emulsifier to formulate a preparation as conventionally employed in the related art field such as emulsifiable concentrates, dusts, aerosols, wettable powders, pellets, oil solutions or fumigants. Examples of the solid carrier or diluent are talc, bentonite, clay, kaolin, diatomaceous earth, vericulite, calcium hydroxide, etc. Examples of the liquid carrier or diluent are benzene, alcohols, acetone, xylene, dioxane, methylnaphthalene, cyclohexanone, etc. As the emulsifier, there may be employed alkylsulfates, alkylsulfonates, arylsulfonates, polyethyleneglycol ethers, polyvalent alcohol esters and the like.

In the preparation, the content of the imidazolidinedione compound (I) may be usually from 0.1 to 95% by weight, preferably from 0.1 to 80% by weight. The preparation may be usually applied in such an amount that 10 to 300 grams of the imidazolidinedione compound (I) are used per 10 are on each application. This application amount may be varied with various factors such as the kind of the imidazolidinedione compound (I), the application mode, the application period, place, the preparation form and the kind of the crop plant to be applied. Examples of the application mode are spraying, perfusing, fumigating, immersing, etc.

It is possible to enhance the useful potency of the imidazolidinedione compound (I) by the simultaneous use of any other insecticides, acaricide, nematocide and/or fungicide. Examples of the co-usable active substances are as follows: allethrin, N-(chrysanthemoxymethyl)-3,4,5,6-tetrahydrophthalimide (i.e. tetramethrin), 5-benzyl-3-furylmethylchrysanthemate (i.e. chrythron), 3-phenoxybenzylchrysanthemate, 5-propargylfurfurylchrysanthemate, 2-methyl-5-propargyl-3-furfurylmethylchrysanthemate. 3-phenoxybenzyl-2,2-dimethyl-3-(2,2-dichlorovinyl)cyclopropanecarboxylate, α-cyano-3-phenoxybenzyl-2',2'-dimethyl-3'-(2,2-dichlorovinyl)cyclopropane carboxylate, α-cyano-3-phenoxybenzyl-2',2',3',3'-tetramethylcyclopropanecarboxylate, α-cyano-3-phenoxybenzyl-2-(4-chlorophenyl)isovalerate, O,O-dimethyl-O-(3-methyl-4-nitrophenyl)phosphorothioate (i.e. sumithion), O,O-dimethyl-O-4-cyanophenylphosphorothioate (i.e. Cyanox), O,O-dimethyl-O-(2,2-dichlorovinyl)phosphate (i.e. DDVP), 2-methoxy-4H-1,3,2-benzodioxaphosphorin-2-sulfide (i.e. Salithion), 1-naphthyl-N-methylcarbamate, 3,4-dimethylphenyl-N-methylcarbamate, 3-methylphenyl-N-methylcarbamate, 2-isopropoxyphenyl-N-methylcarbamate, S-methyl-N-(methylcarbamoyloxy)thioacetimidate, N'-(2-methyl-4-chlorophenyl)-N,N-dimethylformamidine, 1,3-bis(carbamoylthio)-2-(N,N-dimethylamino)propanehydrochloride, N-(3,5-dichlorophenyl)-1,2-dimethylcyclcpropane-1,2-dicarboximide, S-n-butyl-S'-p-tert-butylbenzyldithiocarbonimidate, O,O-dimethyl-O-(2,6-dichloro-4-methylphenyl)phosphorothioate, methyl N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, Polyoxin, Streptomycin, zinc ethylenebis(dithiocarbamate), zinc dimethylthiocarbamate, manganese ethylene-bis(dithiocarbamate), bis(dimethylthiocarbamoyl)disulfide, tetrachloroisophthalonitrile, 8-hydroxyquinoline, dodecylguanidine acetate, 5,6-dihydro-2-methyl-1,4-oxathiine-3-carboxanilide, N'-dichlorofluoromethylthio-N,N-dimethyl-N'-phenylsulfamide, 1-(4-chlorophenoxy)-3,3-dimethyl-1-(1,2,4-triazol-1-yl)-2-butanone, 1,2-bis(3-methoxycarbonyl-2-thioureido)benzene, etc.

Some practical examples of the preparation comprising the imidazolidinedione compound (I) as an active ingredient are shown below, part(s) and % being by weight:

EXAMPLE I (Wettable power)

Twenty-five parts of Compound No. 1, 22 parts of a wetting agent (alkylbenzene sulfonate type) and 53 parts of "Radiolite-200" (diatomaceous earth) were thoroughly pulverized and mixed together to obtain a wettable powder containing 25% of the active ingredient. In application, the wettable powder was diluted with water, and the resulting dilution was sprayed or directly applied.

EXAMPLE II (Emulsifiable concentrate)

Ten parts of Compound No. 1, 40 parts of dimethylsulfoxide, 40 parts of xylene and 10 parts of an emulsifier (polyoxyethylene phenylphenol ether type) were mixed together to obtain an emulsifiable concentrate containing 10% of the active ingredient. In application, the emulsifiable concentrate was diluted with water, and the resulting dilution was sprayed or directly applied.

EXAMPLE III (Oil preparation)

Compound No. 1 (0.2 part) was dissolved in kerosene to make 100 parts of an oil preparation.

EXAMPLE IV (Mixed emulsifiable concentrate)

Twenty parts of Compound No. 1, 20 parts of Sumithion and 10 parts of "Solpol SM-200" ® (Toho Chemical Co., Ltd.) were mixed together to obtain a mixed emulsifiable concentrate.

EXAMPLE V (Aerosol)

Compound No. 1 (0.1 part), 0.2 part of tetramethrin, 7 parts of xylene and 7.7 parts of deodorized oil were mixed. The mixture was filled in an aerosol container having a valve, through which 85 parts of a propellant gas (liquefied petrolic gas) was introduced under pressure to make an aerosol.

EXAMPLE VI (Dust)

Three parts of Compound No. 1 were dissolved in 20 parts of acetone, and 97 parts of talc (300 mesh) were added thereto. After thorough mixing of the material, acetone was evaporated to give a dust.

EXAMPLE VII (Dust)

To 1 part of Compound No. 2, there were added 2 parts of 3-methylphenyl-N-methylcarbamate; the mixture was dissolved in 20 parts of acetone; and 97 parts of talc (300 mesh) was further added thereto. After thorough mixing in a pulverizer, acetone was evaporated to give a dust.

EXAMPLE VIII (Granules)

Five parts of Compound No. 1, 5 parts of "Toyolignin" (lignin sulfonic acid calcium salt) and 90 parts of clay were thoroughly pulverized and mixed together. The mixture was kneaded with water in an amount of 10% with respect to the weight of the mixture, granulated and dried to give granules.

EXAMPLE IX (Emulsifiable concentrate)

Eighty parts of Compound No. 1, 15 parts of "Solpol 355"® (Toho Chemical Co., Ltd.) and 5 parts of xylene were mixed together to give an emulsifiable concentrate containing 80% of the active ingredient. In application, the emulsifiable concentrate was diluted with water, and the resulting dilution was sprayed or directly applied.

In the above Examples, Compound No. 1 may be replaced by any one of Compounds Nos. 2 to 40 so as to obtain a preparation comprising the latter as an active ingredient.

Some test results which show the remarkable insecticidal, acaricidal, nematocidal and fungicidal activities of the imidazolidinedione compounds (I) are given in the following Examples.

EXAMPLE A (Insecticidal activity test on rice stem borer)

Rice plants grown in 1/10000 a Wagner pots and at the tillering stage were inoculated with egg mass of rice stem borer just before hatching. After 4 days, a granular preparation containing the test compound in a concentration of 3% was applied to the pots at a rate of 3 kg/10 a. After 5 days, the stem was cut, and the life and death of the larvae were observed, from which the mortality was calculated. The results are shown in Table 2.

TABLE 2

| Test compound | Mortality (%) |
|---|---|
| Compound No. 12 | 100 |
| Compound No. 14 | 91 |
| Diazinon | 85 |
| Untreated | 4 |

EXAMPLE B (protective activity test on black spot of chinese cabbage (*Alternaria bracissicola*)

When chinese cabbage was grown up to a three leaf stage in a flower pot of 9 cm in diameter, an emulsifiable concentrate of the test compound was diluted with water to a desired concentration and sprayed on the chinese cabbage in a rate of 10 ml per pot. After 4 hours, the leaf surface was inoculated by spraying a spore suspension of *Alternaria bracissicola* which was cultured in an agar medium containing vegetable juice for ten days. After the inoculation, the chinese cabbage was placed in a dark room at 27°-28° C. under a humidity of 100% for 48 hours and then exposed to light. The infectious state was examined on the next day. The degree of damage of the test compound was calculated according to the following equations:

Degree of damage (%) =
$$\frac{\Sigma \text{(Infectious index)} \times \text{(Number of leaves)}}{\text{Total number of leaves} \times 8} \times 100$$

wherein the infectious index was determined on the following criteria:

| Infectious index | Infectious state |
|---|---|
| 0 | No infectious area on leaf |
| 1 | Infectious area of less than 10% |
| 2 | Infectious area of between 10 to 25% |
| 4 | Infectious area of between 25 to 60% |
| 8 | Infectious area of between 60 to 100% |

The results are shown in Table 3, from which it is understood that the imidazolidinedione compounds (I) exhibit a superior disease-prevention effect to the control compound subjected to the same test.

TABLE 3

| Test compound | | Concentration of test compound (ppm) | Degree of damage (%) |
|---|---|---|---|
| Compound No. | 1 | 500 | 0 |
| | 2 | 500 | 1.6 |
| | 3 | 500 | 0 |
| | 4 | 500 | 1.6 |
| | 5 | 500 | 3.1 |
| | 12 | 500 | 6.3 |
| | 13 | 500 | 1.6 |
| | 14 | 500 | 1.6 |
| | 15 | 500 | 0 |
| | 16 | 500 | 3.1 |
| | 18 | 500 | 6.3 |
| | 19 | 500 | 3.1 |
| | 21 | 500 | 0 |
| | 22 | 500 | 13.0 |
| | 23 | 500 | 0.0 |
| | 24 | 500 | 1.6 |
| | 26 | 500 | 1.6 |
| | 27 | 500 | 13.0 |
| | 31 | 500 | 6.3 |
| | 32 | 500 | 6.3 |
| | 33 | 500 | 13.0 |
| | 34 | 500 | 6.3 |
| | 35 | 500 | 1.6 |
| | | 500 | 35.5 |

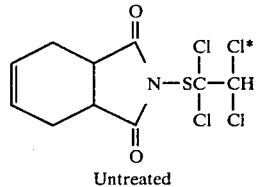

| Untreated | — | 94.0 |

Note:
*Commercially available fungicide.

EXAMPLE C (Preventive effect test on rice blight)

The test compound in the form of an emulsifiable concentration was diluted with water to make a desired concentration and applied to rice plants cultured in pots of 9 cm in diameter and grown up to the 4 or 5-leaved stage at a rate of 10 ml per pot by the use of a spray gun. After one day, the plants were sprayed to inoculate thereon with a spore suspension of *Pyricularia oryzae*. The plants were placed in a room at 24°-26° C. under a humidity of above 90%. Four days thereafter, the infectious area was observed, and the degree of damage was determined therefrom. The disease-preventing effect of the test compound was calculated according to the following equation:

Disease-preventing effect (%) =
$$\frac{\text{Degree of damage in untreated plot} - \text{Degree of damage in treated plot}}{\text{Degree of damage in untreated plot}} \times 100$$

The results are shown in Table 4.

TABLE 4

| Test compound | | Concentration of test compound (ppm) | Disease-preventing effect (%) |
|---|---|---|---|
| Compound No. | 2 | 500 | 100 |
| | 3 | 500 | 88 |
| | 4 | 500 | 100 |
| | 12 | 500 | 100 |
| | 14 | 500 | 100 |
| | 15 | 500 | 100 |
| | 20 | 500 | 100 |
| | 21 | 500 | 100 |
| | 22 | 500 | 100 |
| | 25 | 500 | 93 |
| | 28 | 500 | 100 |
| | 29 | 500 | 98 |
| | 30 | 500 | 95 |
| | 36 | 500 | 100 |
| | 37 | 500 | 100 |
| | 38 | 500 | 100 |
| | 39 | 500 | 100 |
| $(CH_3)_2CHO\!\!\diagdown\!\!P\!-\!SCH_2\!-\!\text{Ph}$ * | | — | 85 |
| $(CH_3)_2CHO\!\!\diagup$ | | | |
| Untreated | | — | 0 |

Note:
*Commercially available fungicide.

EXAMPLE D (Preventive effect on sheath blight)

The test compound in the form of a wettable powder was applied to rice plants cultured in pots of 9 cm in diameter (each pot containing four rice plants) and grown up to 60 cm tall at a rate of 10 ml per pot by the use of a spray gun. After 24 hours, a disc (5 mm in diameter) of mycelium inoculum on a PS synthetic medium was attached onto the sheath, and the plants were placed into a room at 28° C. Four days thereafter, the infectious state at the sheath was observed, and the size of the diseased spot was measured. The degree of damage and the disease-preventing effect were calculated according to the following equations:

$$\text{Degree of damage (\%)} = \frac{\Sigma\left(\text{Infectious index} \times \text{Number of stems}\right)}{\text{Total number of stems} \times 3} \times 100$$

in which the infectious index was determined on the following criteria:

| Infectious index | Infectious state |
|---|---|
| 0 | No infectious spots on sheath |
| 1 | Infectious spot-like part |
| 2 | Infectious spots of less than 3 cm in size |
| 3 | Infectious spots of not less than 3 cm in size |

Disease-preventing effect (%) =
$$\frac{\text{Degree of damage in untreated plot} - \text{Degree of damage in treated plot}}{\text{Degree of damage in untreated plot}} \times 100$$

The results are shown in Table 5.

TABLE 5

| Test compound | | Concentration of test compound (ppm) | Disease-preventing effect (%) |
|---|---|---|---|
| Compound No. | 1 | 500 | 98 |
| | 2 | 500 | 100 |
| | 3 | 500 | 95 |
| | 12 | 500 | 90 |
| | 14 | 500 | 98 |
| | 15 | 500 | 98 |
| | 18 | 500 | 96 |
| | 21 | 500 | 100 |
| | 22 | 500 | 100 |
| | 23 | 500 | 100 |
| | 24 | 500 | 100 |
| | 26 | 500 | 100 |
| Polyoxin* | | 100 fold dilution | 92 |

Note:
*Commercially available fungicide (3.0 %).

EXAMPLE E (Protective effect test on stem rot of cucumber)

When cucumber cultivated in a flower pot of 9 cm in diameter had developed its first true leaf, an emulsifiable concentrate of the test compound was diluted with water and sprayed thereon in a rate of 7 ml per pot. One day after the spraying, the leaves were inoculated with the mycelium disc (5 mm in diameter) of *Sclerotinia sclerotiorum*. Three days thereafter, the infectious state was observed. The degree of infection was examined by measuring the diameter of infectious area, and the degree of damage was calculated according to the following equation:

$$\text{Degree of damage (\%)} = \frac{\text{Mean diameter of infectious area in treated plot}}{\text{Mean diameter of infectious area in untreated plot}} \times 100$$

The results are shown in Table 6, from which it is understood that the imidazolidinedione compounds (I) of the invention exhibit a higher disease-preventing effect than the control compounds.

TABLE 6

| Test compound | | Concentration of test compound (ppm) | Degree of damage (%) |
|---|---|---|---|
| Compound No. | 1 | 500 | 0 |
| | 2 | 500 | 0 |
| | 3 | 500 | 0 |
| | 10 | 500 | 0 |
| | 12 | 500 | 11.9 |
| | 13 | 500 | 3.1 |
| | 14 | 500 | 9.7 |
| | 15 | 500 | 1.9 |
| | 19 | 500 | 3.5 |
| | 21 | 500 | 0 |
| | 22 | 500 | 7.8 |
| | 23 | 500 | 2.4 |
| | 24 | 500 | 1.2 |
| | 26 | 500 | 0.0 |
| 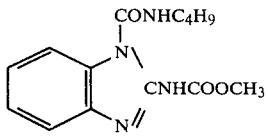 | | 500 | 12.9 |

TABLE 6-continued

| Test compound | Concentration of test compound (ppm) | Degree of damage (%) |
|---|---|---|
| 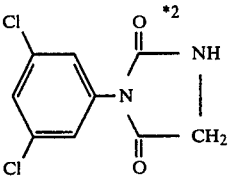 *2 | 500 | 15.0 |
| Untreated | — | (infectious spots being 63 mm in diameter) |

Note: *1 Commercially available fungicide. *2 Compound disclosed in U.S. Pat. No. 3,668,217.

EXAMPLE F (Preventive effect test on canker of apple)

From the new head of an apple tree, two or three branches were cut out and, after elimination of the leaves, washed with water and dried in the atmosphere. Thereafter, the upper and lower parts were cut off, and the central part (which was relatively soft and lignificated) was cut into test pieces of about 12 cm long. For each treatment, 6 to 9 test pieces obtained from 2 to 3 branches were used. Each test piece was immersed in an aqueous dilution of the test compound in an emulsifiable concentrate for 5 minutes and then dried in the atmosphere. After 2 or 3 hours, a disc (5 mm in diameter) of mycelium of *Valsa mali* cultivated on a PSA agar medium was attached onto the section of the cut end, and the resulting piece was kept at 28° C. in a humid room. Eight days from the inoculation, the length of the infectious spot on the test piece was measured, and the degree of damage was calculated according to the following equation:

$$\text{Degree of damage (\%)} = \frac{\text{Length of infectious spot in average in treated plot}}{\text{Length of infectious spot in average in untreated plot}} \times 100$$

From the degree of damage, the disease-preventing effect was calculated according to the following equation:

$$\text{Disease-preventing effect (\%)} = \frac{\text{Degree of damage in untreated plot} - \text{Degree of damage in treated plot}}{\text{Degree of damage in untreated plot}} \times 100$$

The results are shown in Table 7.

TABLE 7

| Test compound | | Concentration of test compound (ppm) | Disease-preventing effect (%) |
|---|---|---|---|
| Compound No. | 1 | 1000 | 95 |
| | 2 | 1000 | 98 |
| | 3 | 1000 | 100 |
| | 4 | 1000 | 92 |
| | 12 | 1000 | 92 |
| | 14 | 1000 | 90 |
| | 15 | 1000 | 93 |
| | 16 | 1000 | 94 |
| | 18 | 1000 | 90 |
| | 21 | 1000 | 98 |
| | 22 | 1000 | 96 |
| | 23 | 1000 | 98 |
| | 36 | 1000 | 94 |
| | 37 | 1000 | 94 |
| *1 | | 1000 | 12 |
| *2 | | 1000 | 60 |
| Untreated | | — | 0 |

Note:
*1 Compound disclosed in U.S. Pat. No. 3,716,552.
*2 Compound disclosed in U.S. Pat. No. 3,668,217.

EXAMPLE G (Acaricidal activity test on carmine mite)

Seedlings of kidney beans after 9 days from seeding in flower pots were each inoculated with 10 female adults of carmine mite (*Tetranychus cinnabarinus*) per leaf and allowed to stand in a greenhouse kept at 27° C. for 1 week. The test compound in the form of an emulsifiable concentrate was diluted with water and applied to the pots at a rate of 10 ml per pot by spraying. After 1 week from the spraying, the damage was observed on the following criteria:

—: no damage
+: slight damage
++: considerable damage
+++: remarkable damage

Also, the number of the survived adults was counted. The results are shown in Table 8.

TABLE 8

| Test compound | Concentration of test compound (ppm) | Damage | Number of survived adults |
|---|---|---|---|
| 3 | 500 | — ~ + | 13 |
| 10 | 500 | — ~ + | 19 |
| 11 | 500 | — | 0 |
| 12 | 500 | — | 0 |
| 14 | 500 | — | 8 |
| 19 | 500 | — | 0 |
| 28 | 500 | — ~ + | 25 |
| 31 | 500 | — | 7 |
| 33 | 500 | — | 10 |
| 37 | 500 | — | 0 |
| 38 | 500 | — ~ + | 18 |
| Chlordimeform* | 500 | — ~ + | 21 |
| Untreated | — | +++ | 457 |

Note:
*50% emulsion.

EXAMPLE H (Killing effect test on *Panagrellus redivivus*)

A 40% emulsion of the test compound was diluted with water to 2000 ppm. The dilution (10 ml) was charged in a 20 ml volume beaker, and a solution (0.5 ml) containing a number of *Panagrellus redivivus* was admitted thereto. After 48 hours, observation was made microscopically to examine the mortality, and the judgement of the effect was made on the following criteria:

—: mortality of less than 50%
+: mortality of 50 to 90%
++: mortality of more than 90%

The results are shown in Table 9.

TABLE 9

| Test compound | Judgement |
|---|---|
| 3 | ++ |
| 7 | ++ |
| 8 | ++ |
| 9 | ++ |
| 11 | ++ |
| 12 | ++ |
| 13 | ++ |
| 14 | ++ |
| 23 | ++ |
| 30 | ++ |
| 37 | ++ |
| 38 | ++ |
| 39 | ++ |
| Untreated | — |

What is claimed is:

1. A compound of the formula:

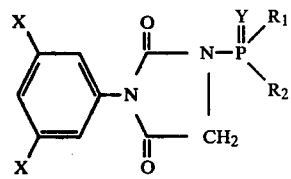

wherein X is a chlorine atom or a bromine atom, Y is an oxygen atom or a sulfur atom, and $R_1$ and $R_2$ are each a $C_1$-$C_4$ alkyl group, a $C_1$-$C_4$ alkoxy group, a $C_1$-$C_4$ alkylthio group, an ar($C_1$-$C_4$)alkylthio group, a $C_1$-$C_4$ alkoxy($C_2$-$C_4$)alkoxy group, a phenyl group, a phenoxy group, a $C_1$-$C_4$ alkylthiophenoxy group, a $C_1$-$C_8$ alkylamino group, a $C_2$-$C_8$ alkenylamino group or a cyano($C_1$-$C_4$)alkylamino group.

2. The compound according to claim 1, wherein X is a chlorine atom and $R_1$ and $R_2$ are each a $C_1$-$C_4$ alkoxy group, a $C_1$-$C_4$ alkylthio group, an ar($C_1$-$C_4$)alkylthio group, a $C_1$-$C_4$ alkoxy($C_2$-$C_4$)alkoxy group or a phenyl group.

3. The compound according to claim 1, wherein X is a chlorine atom, Y is an oxygen atom and $R_1$ and $R_2$ are each an ethoxy group.

4. The compound according to claim 1, wherein X is a chlorine atom, Y is a sulfur atom, $R_1$ is a phenethylthio group and $R_2$ is an ethoxy group.

5. The compound according to claim 1, wherein X is a chlorine atom, Y is a sulfur atom, $R_1$ is a sec-butylthio group and $R_2$ is an ethoxy group.

6. The compound according to claim 1, wherein X is a chlorine atom, Y is a sulfur atom, $R_1$ is an n-propylthio group and $R_2$ is an ethoxy group.

7. An insecticidal, accaricidal, nematocidal or fungicidal composition which comprises as an active ingredient an effective amount of the compound according to claim 1 and an inert carrier.

8. The composition according to claim 7 for insecticidal use.

9. The composition according to claim 7 for fungicidal use.

10. A method for controlling insects, acarids, nematodes or fungi which comprises applying an effective amount of the compound according to claim 1 to the insects, acarids, nematodes or fungi.

11. The method according to claim 10 for controlling insects.

12. The method according to claim 10 for controlling fungi.

13. The method according to claim 12 wherein the fungi are *Valsa mali*.

* * * * *